(12) United States Patent
Connerton

(10) Patent No.: US 7,491,387 B2
(45) Date of Patent: Feb. 17, 2009

(54) DISINFECTION OF FOODSTUFFS

(75) Inventor: Ian Frank Connerton, Loughborough (GB)

(73) Assignee: The University of Nottingham, Nottingham (GB)

( * ) Notice: Subject to any disclaimer, the term of this patent is extended or adjusted under 35 U.S.C. 154(b) by 127 days.

(21) Appl. No.: 11/367,967

(22) Filed: Mar. 3, 2006

(65) Prior Publication Data
US 2006/0222632 A1    Oct. 5, 2006

Related U.S. Application Data

(63) Continuation of application No. PCT/GB2004/003775, filed on Sep. 6, 2004.

(30) Foreign Application Priority Data
Sep. 5, 2003   (GB) .................. 0320838.6

(51) Int. Cl.
*A01N 63/00*   (2006.01)
*G01N 33/53*   (2006.01)
*C12Q 1/70*    (2006.01)

(52) U.S. Cl. .................. 424/93.6; 435/7.32; 435/5

(58) Field of Classification Search .................. None
See application file for complete search history.

(56) References Cited

U.S. PATENT DOCUMENTS 6,399,097 B1   6/2002   Fischetti et al.

FOREIGN PATENT DOCUMENTS

| WO | WO 01/50866 A  |   | 7/2001 |
| WO | WO 02/007742   |   | 1/2002 |
| WO | WO 02/07742    | * | 1/2002 |
| WO | WO 03/000274   |   | 1/2003 |
| WO | WO 03/020958 A |   | 3/2003 |

OTHER PUBLICATIONS

Waegnaar et al., "Phage Therapy Of *Campylobacter Jejuni* Colonisation In Broilers,"Journal of Medicinal Microbiology, 2001, vol. 291, No. Suppl. 31, p. 92-93, article 5-29.*
Sails, et al. Characterizaion of 16 *Campylobacter jujuni* and *c. coli* Typing Bacteriophages: J Med. Microbiol. 1998; 47(2) p. 123-128.*
Brown, et al. Frequency and Spatial Distribution of Environmental Campylobacter spp. Appl. Environ. Microbiol, 2004, vol. 70, No. 11, p. 6501-6511.*
Grawjewski et al. Development of a bacteriophage typing scheme form *Campylobacter jujuni* and *Camplyobacter coli*. Epidemiol. Infect. 1985; 104:403-414.*
Goode, et al. Reduction of Experimental Salmonella and Campylobacter Contamination of Chicken Skin by Application of Lytic Bacteriophages. Appl. Environ. Microbiol. 2003; 69(8):5032-5036.*
Connerton et al., "Longitudinal study of *campylobacter jejuni* bacteriophages and their hosts from broiler chickens," Applied and Environmental Microbiology, vol. 70, No. 7, Jul. 2004, pp. 3877-3883, XP002313914, ISSN: 0099-2240.
Sails et al., "Characterisation of 16 *Campylobacter Jejuni* and *C. Coli* Typing Bacteriophages," Journal of Medical Microbiology, Harlow, GB, vol. 47, No. 2, Feb. 1998, pp. 123-128, XP008002815, ISSN: 0022-2615.
Atterbury, Robert J. et al., "Isolation and Characterization of Campylobacter bacteriophages from retail poultry," Applied and environmental Microbiology, col. 69, No. 8, Aug. 2003, pp. 4511-4518, XP002313915, ISSN: 0099-2240.
Atterbury et al., "Isolation and Characterization of Campylobacter Bacteriophages from Retail Poultry," Applied and Environmental Microbiology, Aug. 2003, p. 4511-4518.
Waegnaar et al., "Phage Therapy Of *Campylobacter Jejuni* Colonisation In Broilers," Journal of Medicinal Microbiology, 2001, vol. 291, p. 92-93, article J-29.

* cited by examiner

*Primary Examiner*—Mary E. Mosher
*Assistant Examiner*—Bo Peng
(74) *Attorney, Agent, or Firm*—Baker Botts LLP

(57) ABSTRACT

A method of disinfection of livestock is provided. The method comprises administering at least one bacteriophage in an effective amount to said livestock to reduce the number of *Campylobacter spp* present in the gastro-intestinal tract of said livestock. The bacteriophage are selected from CP8 (NCIMB Accession No. 41184) and CP34 (NCIMB Accession No. 41185).

12 Claims, 2 Drawing Sheets

DISINFECTION OF FOODSTUFFS

This application is a continuation of International Application Serial No. PCT/GB2004/003775, filed Sep. 6, 2004, published Mar. 17, 2005, which claims priority from Great Britain Application Serial No. 0320838.6, filed Sep. 5, 2003, each of which are incorporated by reference in their entireties herein, and from which priority is claimed.

This invention relates to the use of bacteriophage in the disinfection of foodstuff, and in particular, but not exclusively to, livestock or foodstuff contaminated with *Campylobacter spp*, a method of using said bacteriophage for disinfection and bacteriophage for use in such a method.

*Campylobacter spp.* is a major cause of food-borne diarrhoeal disease. Persistent *Campylobacter spp.* contamination of poultry meat is a significant problem to producers and retailers alike. It is known that poultry acts as a reservoir for this pathogen; a large percentage (approximately 60 to 80%) of birds harbour *Campylobacter jejuni* in their intestinal tracts.

In broiler chickens the *Campylobacter* species are commensal organisms, rather than being an infection. Colonisation of the bird's gastro-intestinal tract occurs at an early age, for example through contamination of drinking water or from the environment. Horizontal transfer thereafter within the broiler house wherein the chickens are kept is progressive and rapid, such that the whole flock will be infected before slaughter.

The birds are often starved before slaughter, which reduces the faecal shedding of *Campylobacter spp*, but can result in greater numbers in the carcass. It is an aim of the present invention to reduce the levels of *Campylobacter jejuni* and/or *Campylobacter coli* present in the birds before slaughter and present on the resultant poultry meat.

Accordingly, the present invention provides a method of disinfection of livestock comprising administering at least one bacteriophage in an effective amount to said livestock to reduce the number of *Campylobacter spp.* present in the gastrointestinal tract of said livestock.

*Campylobacter spp.* are commensal organisms that do not affect livestock (especially poultry and game) accordingly the present invention is not concerned with treating any disease present in the livestock.

It is an advantage of the present invention to use the bacteriophage for prophylactic phage therapy, i.e. the bacteriophage are administered to chickens prior to slaughter in order to reduce the numbers of *Campylobacter spp* species contaminating the poultry meat and entering the human food chain.

At least one of the bacteriophage is from the family, Myoviridae. Preferably the bacteriophage is selected from the group consisting of CP8 (NCIMB ACCESSION NO. 41184) and CP34 (NCIMB ACCESSION NO. 41185).

The or each bacteriophage are administered to livestock at a range of between $10^2$ to $10^9$ pfu/ml$^{-1}$. Preferably the bacteriophage are administered to livestock at $10^5$ pfu/ml$^{-1}$.

The livestock are preferably chickens. In particular the livestock are broiler chickens. Alternatively the livestock is selected from the group consisting of ducks, turkeys, pigs, cattle, goats and sheep.

The or each bacteriophage are preferably administered orally via an antacid solution and most preferably in the livestock drinking water.

The or each bacteriophage are administered between 1 and 4 days before slaughter. Preferably the or each bacteriophage are administered 2 days before slaughter.

The *Campylobacter spp.* is preferably *Campylobacter jejuni*. Alternatively the *Campylobacter spp.* is *Campylobacter coli*.

The present invention also provides a method of disinfecting foodstuff comprising administering at least one bacteriophage in an effective amount to foodstuff to reduce the number of *Campylobacter spp.* in said foodstuff.

At least one of the bacteriophage is from the family, Myoviridae.

Preferably at least one of the bacteriophage is selected from the group consisting of CP8 (NCIMB ACCESSION NO. 41184) and CP34 (NCIMB ACCESSION NO. 41185)

The or each bacteriophage are administered to foodstuff at a range of between $10^2$ to $10^9$ pfu/ml$^{-1}$. Preferably the or each bacteriophage are administered to a foodstuff at $10^5$ pfu/ml$^{-1}$.

The foodstuff is preferably fresh poultry meat. Alternatively, the foodstuff is frozen poultry meat.

The foodstuff may also be selected from the group consisting of fresh or frozen beef, lamb, duck, turkey, pork or goat.

The *Campylobacter* spp. is preferably *Campylobacter jejuni*. Alternatively, the *Campylobacter spp.* is *Campylobacter coli*.

The present invention also provides a method of selecting bacteriophage suitable for reducing the numbers of *Campylobacter spp.* in livestock or foodstuff, which method comprises the steps of:

isolating material containing bacteriophage; and selecting bacteriophage that bind to *Campylobacter spp.*

The present invention further provides the isolated bacteriophage CP8 (NCIMB ACCESSION NO. 41184).

The present invention further provides the isolated bacteriophage CP34 (NCIMB ACCESSION NO. 41185).

The present invention further provides the use of isolated bacteriophage CP8 (NCIMB ACCESSION NO. 41184) as a disinfectant in accordance with the invention.

The present invention further provides the use of isolated bacteriophage CP34 (NCIMB ACCESSION NO. 41185) as a disinfectant in accordance with the invention.

The present invention further provides a kit comprising:

a) at least one isolated bacteriophage in accordance with the present invention;

and optionally b) instructions for using the kit.

At least one of the bacteriophage is preferably selected from the group consisting of CP8 (NCIMB ACCESSION NO. 41184) and CP34 (NCIMB ACCESSION NO. 41185).

Optionally, the kit contains apparatus for administering the bacteriophage to livestock or foodstuffs. The apparatus is preferably a spray pump dispenser, an aerosol or a pipette.

Optionally, the kit contains one or more buffers for preparing the bacteriophage. The or each buffer is preferably selected from a storage buffer and a dispensing buffer. The storage buffer comprises 100 mM NaCl, 10 mM MgSO$_4$, 20 mM Tris pH7.4 and 0.1% gelatin.

The present invention will now be described merely by way of example with reference to the examples and following Figure:

1. Materials and Methods

Figure 1A:
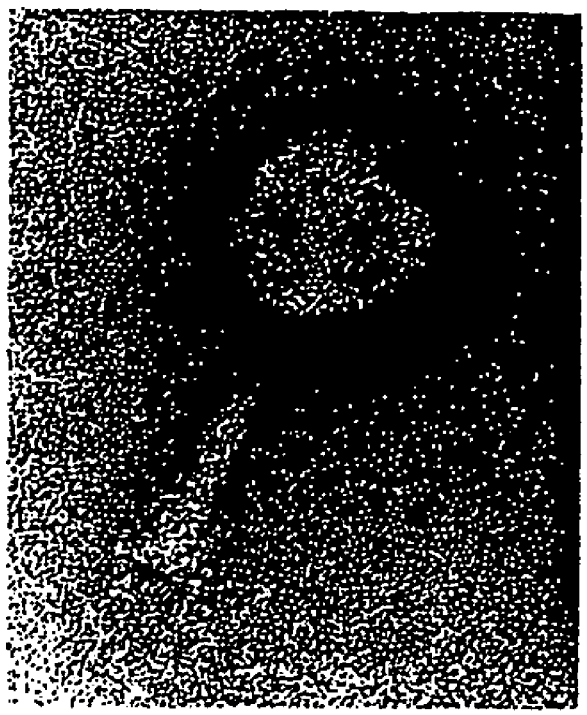
FIG. 1(*a*) is an electron micrograph of isolated bacteriophage CP8 (NCIMB ACCESSION NO. 41184).
FIG. 1(b) is an electron micrograph of bacteriophage CP34 (NCIMB ACCESSION NO. 41185)

The method used for isolation of bacteriophage from poultry samples was developed by modification of both the methods described by Gradjewski et al., (1985) and Salama et al., (1989).

Isolation of *Campylobacters* from chicken faeces, cloacal swabs and chicken carcasses to use as host bacteria for bacteriophage isolation *Campylobacter spp.* was isolated from chickens by direct plating using modified CCDA agar. Dilutions were made in Maximum Recovery Diluent (MRD,; Oxoid No. CM 733). Plates were incubated at 42° C. for 48 h under microaerobic conditions (5% oxygen). Colonies were confirmed as being *Campylobacter spp.* by having typical colony morphology, typical cell morphology (by Gram stain), and for being oxidase and catalase positive. A hippurate hydrolysis test was performed to distinguish *C. jejuni* from other *Campylobacter spp.*

Preparation of Host Bacteria Lawn for Bacteriophage Isolation

Host bacteria for bacteriophage isolation were grown as lawns on blood agar plates (5% defibrinated horse blood in Blood Agar base No 2) incubated microaerobically for 18 h at 42° C. The bacteria were scraped off using a sterile swab and suspended in ice cold 10 mM $MgSO_4$. For each lawn, 100 µl of cell suspension was added to 5 ml of liquid NZCYM overlay medium (0.6% Select agar in NZCYM broth) held at 45° C. and poured immediately onto a pre-warmed NZCYM agar (1.2% Select agar in NZCYM broth with 10 µg/ml Vancomycin). The plates were allowed to set for 10 min then dried at 42° C. for 30 min face down with the lids open. Each sample for bacteriophage isolation was applied as a 10 µl spot to the prepared lawn.

Preparation of Samples for Isolation of Phage From Excreta/Cloacal Swabs using Prepared Host Bacteria Lawn A 10% suspension of excreta was prepared in SM buffer (100 mM NaCl, 10 mM $MgSO_4$, 20 mM Tris pH 7.4, 0.1% gelatin). Cloacal swabs were emulsified in 2 ml of SM buffer. After 24 h incubation at 4° C. (to allow phage to dissociate), 1 ml of this suspension was centrifuged at 3,000 rpm for 5 minutes to remove debris. The supernatant was transferred to a new tube and centrifuged at 13,000 rpm to remove bacteria. The resulting supernatant was filtered through a 0.2 µm filter to remove any remaining bacteria. The filtrate was then spotted onto bacterial lawns prepared as above. The filtrate was also spotted onto a bacterial lawn of the universal permissive strain *C. jejuni* PT14 (NCTC 12662), prepared as above. The phage suspension was allowed to absorb into the top-agar for approximately 30 minutes at room temperature. The plates were then incubated for 24 h at 42° C. under microaerobic (5% $O_2$) conditions.

Collection of Bacteriophage Following Incubation on Host Lawns and Plaque Purification by the Pour Plate Method Single bacteriophage plaques were extracted from the overlay using a pipette tip and suspended in 200 µl of SM medium. Bacteriophage were propagated by adding 10 µl of the single plaque phage suspension to 100 µl of host bacteria cell suspension. Bacteriophage were allowed to absorb for 30 minutes at 42° C. This suspension was then added to molten top agar and poured over the surface of a pre-warmed NZCYM plate. Once set the plate was incubated for 24 h at 42° C. under microaerobic (5% $O_2$) conditions.

A single plaque was then collected into 200 µl of SM and the whole procedure repeated a total of 3 times.

2. Characterisation and Selection of Bacteriophage

First stage Amplification to Enable Characterisation and Selection

Ten pour plates for each bacteriophage were prepared exactly as for the plaque purification (above) using the final plaque collected. Following incubation, 5 ml of SM buffer was added to each plate. The plates were then gently shaken for 16 h at 4° C. to wash the bacteriophage off the surface of the plates. The resultant bacteriophage suspension was collected and filtered through a 0.2 µm filter to remove bacteria. The bacteriophage titre of this suspension was determined using the Miles and Misra technique and was found to be around $10^8$ pfu/ml (plaque forming units/ml).

Characterisation and Selection

The lytic spectrum of each new bacteriophage was determined by spotting 10 µl of each bacteriophage onto bacterial lawns of a bank of test *Campylobacter* strains. These strains included NCTC reference strains, strains with known phage type (PT strains), broiler isolates, free range chicken isolates, isolates from poultry meat and from human faecal samples. Only bacteriophage showing confluent lysis on a wide range of strains were selected as candidates for the trial. Some phage have been found to behave poorly in the trials despite having a wide host range. These have been eliminated from the stocks of potentially useful phage.

Stability

The stability of the selected bacteriophage was assessed by periodic titration of material held at 4° C. in SM buffer. Titres dropped by more than 2-logs following lyophilisation so this method of preservation was not pursued further. The titres of some of the bacteriophage were found to drop rapidly by several logs even at 4° C. in SM buffer. Only those bacteriophage that maintain their titre over 3 months at 4° C., in SM buffer, were selected.

Binding of Bacteriophage to Non-Specific Material

Phage from both broiler chicken and poultry meat sources were found to vary significantly in their ability to adhere to surfaces (plastic) and (non-specifically) to bacteria which will not support their replication. Phage displaying non-specific adherence will be ineffective for the application of phage therapy. Phage were therefore selected on the basis of their efficient recovery from plastic surfaces to initiate infection of *Campylobacter*, and their recovery after exposure to non-permissive bacteria and membrane vesicles generated by these bacteria.

Pulsed Field Gel Electrophoresis

*Campylobacter* bacteriophage have unusually large genomes (Sails et al., 1998). Despite this their DNA is resistant to a large number of restriction enzymes (an essential survival mechanism for phage). Characterisation and discrimination of phage using molecular methods is therefore difficult. Sails et al., (1998) reported that the phage used in their study fell into 3 classes based on genome size (determined by PFGE). PFGE was used to characterise the newly isolated phage from poultry and determine their genome sizes. The sizes of all the broiler isolates were approximately 130 kb. These phage fall into class III of the grouping advanced by Sails et al., (1998). However some phage isolated from poultry meat were around 180 kbp and belonged to group II.

Electron Microscopy

Figure 1A:
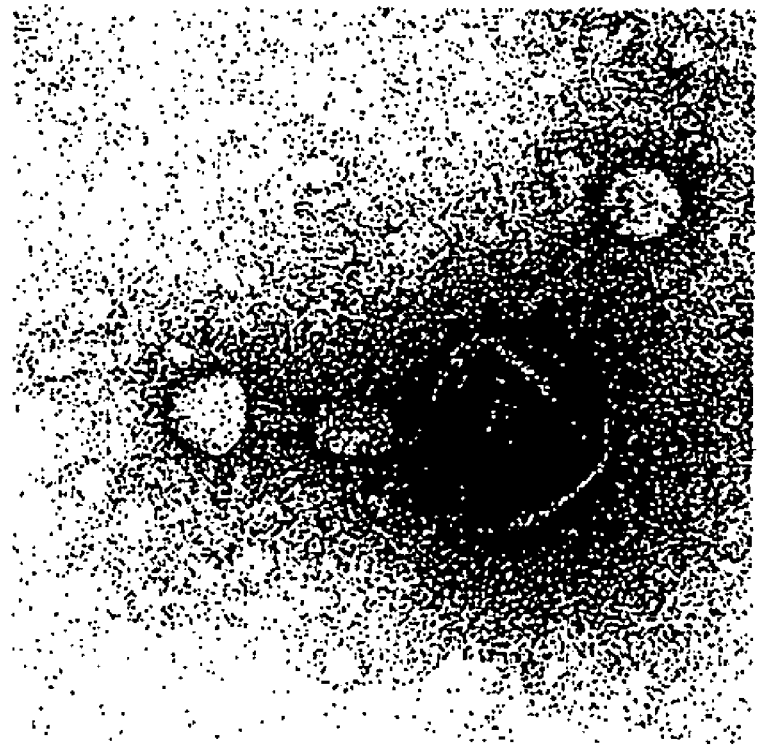
Figure 1B:

Electron micrographs of the phage (FIGS. 1 a and b) have so far revealed all the phage from broiler chickens to be similar to those examined by Sails et al., (1998) having icosahedral heads with long contractile tails and belonging to the family Myoviridae. The larger phage isolated from poultry meat were from the same family but had distinctive collar structure.

3. Bulk Production of the Most Suitable Bacteriophage in the Laboratory

The growth from an overnight blood agar plate culture of appropriate strain was suspended in 2 ml of 10 mM $MgSO_4$. One ml of this bacterial suspension was added to a 150 ml conical flask containing 40 ml of Nutrient Broth No 2 (CM 67). To this, 100 μl of approximately $10^8$ pfu/ml phage was added. The flask was placed in a gas jar under microaerobic conditions and incubated with shaking at 100 rpm at 42° C. for 48 h. Bacterial debris was removed by centrifugation and filtration through a 0.2 μm filter. The titre of the bacteriophage suspension was approximately $10^9$ pfu/ml.

Concentration of Bacteriophage by Centrifugation

Bacteriophage were then collected by centrifugation at 40,000 g for 2 h at 4° C. The pellets were resuspended in 10 mM sodium phosphate buffer pH7.0 (a suitable buffer for feeding to chickens). The titre of this concentrated bacteriophage was usually around $10^{10}$ pfu/ml. Stability in this buffer at 4° C. was found to be equivalent to that of SM buffer i.e. very little decline in viability over a period of 3 months. Batches of up to 1 litre can be prepared by scaling up the procedure.

4. Monitoring

Resistance to Phage

Selection of phage resistant *Campylobacter* strains was envisaged as a possible problem to the use of phage therapy. Bacteria develop resistance to phage by spontaneous mutation and phage resistant colonies are visible after prolonged incubation at a high multiplicity of infection. None of the *Campylobacter* strains isolated in the example 1 (see below) were resistant to CP8 (NCIMB ACCESSION NO. 41184) (although resistant colonies could be produced by mixing phage and bacteria in vitro). It was, however, possible to isolate CP34 (NCIMB ACCESSION NO. 41185) phage resistant colonies in the phage-treated but not the untreated birds from example 2 (see below). In order to establish the frequency of resistance to CP34 (NCIMB ACCESSION NO. 41185) post-intervention, 10 colonies from the isolation plates from each bird were selected and tested for resistance to CP34 (NCIMB ACCESSION NO. 41185). During the first 3 days post-intervention no resistant *Campylobacter* strains were detected. However, on the 4$^{th}$ and 5$^{th}$ days, 2 out of 10 single-colony isolates recovered from a single phage treated bird demonstrated phage resistance. There was no correlation between birds having higher than average counts of *Campylobacter* and the isolation of resistant colonies.

This together with the low frequency of resistance (20% or less) add weight to earlier observations that acquisition of phage resistance is associated with a reduced competitive advantage.

To further investigate the nature of resistance to phage and establish if resistant variants were as efficient at colonisation as the parent strain, two resistant isolates of HPC5 (HPC5-14 and HPC5-20) were used to re-colonise birds. It was noted that these strains grew poorly on blood agar plates giving small discrete colonies but retained motility. The results showed that whilst colonisation was achieved over 5 days, *Campylobacter* colony isolates recovered from these birds had regained their sensitivity to phage CP34 (NCIMB ACCESSION NO. 41185) indicating a strong selection pressure against phage resistance in vivo. This experiment demonstrates that, although phage resistance may occur, at least with this phage/host combination, it is not likely to significantly reduce the effectiveness of the treatment. The resistant variants appear to be less fit and must revert back to being sensitive to colonise efficiently, and as the phage also probably persist these sensitive strains will once more be vulnerable to attack. Application of phage just prior to slaughter is envisaged as the best way to avoid problems associated with developing phage resistance within the broiler house.

Presence and Survival of Phage on Retail Chicken

The recovery of phage, from spiked chicken samples was investigated over an 11 day period at 4° C. using the methods of Atterbury et al. (2003). The recovery remained constant between 40-44% of the inoculated titre over a 7-day period. On day 7 there was a decrease in titre of from 44% to 35%. This decrease continued for the duration of the time course until reaching 19% at the end of the study. This contrasts with recovery of phage from frozen chicken where initial recovery was close to 100% but rapidly fell to 22% a day after inoculation. Recovery thereafter was in the range 22 to 28%.

The limit of phage detection was found to be $2 \times 10^3$ pfu per 10 $cm^2$ area of chicken skin.

Bacteriophage are therefore naturally present on the surface of poultry and can survive for relatively long periods in the absence of a replicating host and even survive freezing at −20° C. Bacteriophage will remain active against the *Campylobacter* present on chicken skin and are capable of reducing surface contamination (see example 3).

Obtaining Segments of Phage Genomic Nucleotide Sequence

Genomic DNA from phage were digested with restriction enzyme DraI and ligated into pUC18 plasmid (Ready to Go, Pharmacia). Following transformation plasmids with DNA inserts were sequenced using M13 forward (sequence I.D. No. 8) and reverse primers (sequence I.D. No. 9) and the sequence compared to DNA databases. The translation of the sequences was also compared to protein databases. The databases used are well known to those of skill in the art. Whilst most inserts contained DNA clearly originating from the *Campylobacter*, host unique sequences were obtained that appeared to be phage derived. Cloning phage DNA is extremely problematic due to extensive substitution and modification of bases, which prevents replication in the *E. coli* host. Primers (see table 1 and accompanying sequence listing) were designed based on the presumptive phage sequences and these were used to amplify DNA from the bacteriophage isolates. One of these primer pairs readily amplify product from CP8 (NCIMB ACCESSION NO. 41184) genomic DNA but not from any other phage and represents a method to distinguish CP8 (NCIMB ACCESSION NO. 41184) and like phage. These primers are useful for tracking CP8 (NCIMB ACCESSION NO. 41184) phage through the post treatment, slaughter, preparation and storage phases as they distinguish the test phage from any naturally occurring bacteriophage found on the surface of poultry meat.

TABLE 1

| Phage Sequence | Sequence ID No. | Primers | Sequence ID No. |
|---|---|---|---|
| CP8-85 | 1 | CPPP1 | 2 |
|  |  | CPPP2 | 3 |

TABLE 1-continued

| Phage Sequence | Sequence ID No. | Primers | Sequence ID No. |
|---|---|---|---|
| CP8-92 | 4 | CPPP3 | 5 |
|  |  | CPPP4 | 6 |
| CP8-93 | 7 | M13F | 8 |
|  |  | M13R | 9 |

It will be appreciated that cloning DNA from these bacteriophages is difficult. This is due to high levels of methylation and substitution which serve to protect the bacteriophage genome from restriction endonucleases present in bacteria.

As such only small DNA fragments were cloned. No significant homologies were found when DNA sequence and protein sequence databases were searched using the isolated cloned DNA.

EXAMPLE 1

Use of CP8 (NCIMB ACCESSION NO. 41184) Phage to Reduce Campylobacters in Chickens A low passage broiler chicken isolate, C. jejuni GII C8 (Phage type: 35; Heat-Stable Serotype: untypable), was selected to use as the colonisation strain because it was sensitive to CP8 (NCIMB ACCESSION NO. 41184) and was typical of the strains isolated from broiler houses. The groups were as described in Table 1. The birds were split into 4 groups (n=10 birds each) depending on infection regime and controls used. Birds in group 1 were uninfected controls. Birds in groups 3 and 4 were infected at day 22 with $10^8$ cfu C. jejuni GII C8. Birds in groups 2 and 3 were administered with $5 \times 10^8$ pfu CP8 (NCIMB ACCESSION NO. 41184) in 30% $CaCO_3$ (antacid) on day 25. Two birds from each group were sacrificed each day for 5 days. The sample sites on sacrificed birds included: crop, gizzard, small intestine, large intestine, caeca, muscle and organs including liver, pancreas, brain and heart. Phage and Campylobacter were enumerated. The Campylobacter negative control birds remained negative throughout the trial showing that sufficient containment measures had been achieved. A summary of the results of this experiment is given in Table 1. Excreta samples showed that the test birds were colonised with Campylobacter to approximately $10^7$ cfu/ml by the time phage were administered (within 3 days). Campylobacter was only isolated from the digestive system of the birds not from any other organs.

TABLE 1

Summary of intervention with phage showing the average number of Campylobacters recovered from the caecal contents per day

| Day | Campylobacter Control group: (Average cfu/g) GROUP4 | Phage + Campylobacter group: (Average cfu/g) GROUP3 |
|---|---|---|
| 1 | $1.6 \times 10^7$ | $<10^2$ |
| 2 | $2.5 \times 10^8$ | $<10^2$ |
| 3 | $7.6 \times 10^8$ | $4.0 \times 10^5$ |
| 4 | $5.6 \times 10^7$ | $2.5 \times 10^7$ |
| 5 | $2.1 \times 10^7$ | $3.1 \times 10^7$ |

These results indicate a large reduction in numbers of Campylobacter for 2 days post phage treatment. After this time the numbers increased to a level comparable to controls on days 4 and 5. The re-colonising Campylobacter isolates from this experiment were not phage resistant and could be shown to be genotypically identical to the initial colonising strain (fla type).

EXAMPLE 2

Use of CP34 (NCIMB ACCESSION NO. 41185) Bacteriophage to Reduce Numbers of Campylobacters in Chickens and Determination of Optimum Dose for This Bacteriophage A broiler phage isolate CP34 (NCIMB ACCESSION NO. 41185), was selected for 2 reasons:
1) It had a broad host range against broiler house isolates similar to CP8 (NCIMB ACCESSION NO. 41184).
2) The availability of C. jejuni strain HPC5 (Heat-Stable Serotype UT; Phage type: RDNC-reacts with phage but does not conform to a designated phage type) that was isolated at the same time as phage CP34 (NCIMB ACCESSION NO. 41185) and which had previously been used in the colonisation trial to determine its colonisation potential. This strain was used to propagate phage CP34 (NCIMB ACCESSION NO. 41185) in the laboratory minimising potential host restriction.

The intervention experiment was carried out in the same way as in the previous example. Briefly, chickens were infected with $10^9$ cfu C. jejuni HPC5 at 20 days old (2 days earlier than previously to follow the numbers of Campylobacters in the controls for a longer period prior to the phage administration). Phage were administered at a range of doses ($10^5$ pfu, $10^7$ pfu and $10^9$ pfu) in 30% $CaCO_3$ (antacid) at 25 days old. The titres of both phage and bacteria in sacrificed birds were followed for 5 days and compared to controls colonised with C. jejuni HPC5. In the first 24 h following intervention there was a sharp 4 log decline in Campylobacter titre in the caeca with the $10^5$ and $10^7$ dosage and a 2 log decline in the upper and lower intestine in the phage treated birds compared to the controls. The highest dose of phage ($10^9$ pfu) was unexpectedly the least effective in the first 24 h but still resulted in a greater than 2 log decline in the Campylobacter titre in caeca of phage treated birds compared to controls 48 h following treatment.

The results show a reproducible decline in numbers of Campylobacter by at least 2 logs for CP34 (NCIMB ACCESSION NO. 41185), a sharp initial decline which was maintained over 4 to 5 days. A dose of between $10^5$ pfu and $10^7$ pfu was found to be optimum in this experiment. The number of phage peaked at approximately $10^7$ pfu/g in the upper and lower intestine at 27 days and in the caeca at 29 days. There was no correlation between initial dose and numbers of phage isolated following phage treatment. All samples contained between $10^5$ and $10^8$ pfu/g. The high peaks of phage correspond roughly to the minimum troughs of the bacteria as might be expected of a host prey relationship. The number of Campylobacter then began to rise which corresponds to falling numbers of phage. This had been anticipated and confirms our original assumption that appropriate timing of intervention (prior to slaughter) is critical to get maximum benefit.

The Campylobacter negative control birds remained negative throughout the trial showing that sufficient containment measures had been achieved. A summary of the results of this experiment with phage CP34 (NCIMB ACCESSION NO. 41185) is given in Table 2 and compared with the previously reported results for phage CP8 (NCIMB ACCESSION NO. 41184). The initial reduction in the numbers of colonising Campylobacter with CP34 (NCIMB ACCESSION NO. 41185) phage were not as great as had been observed with the phage CP8 (NCIMB ACCESSION NO. 41184) where greater than a 5 log drop in number of Campylobacter was observed.

This comparison illustrates the importance of careful phage selection to the success of intervention.

TABLE 2

Summary CP34 (NCIMB ACCESSION NO. 41185) intervention compared with CP8 (NCIMB ACCESSION NO. 41184) trial showing the average number of *Campylobacters* recovered from the caecal contents per day CP8 (NCIMB ACCESSION NO. 41184) Trial with GIIC8 host

| Day | *Campylobacter* Control group: (Average cfu/g) | Phage + *Campylobacter* group: (Average cfu/g) |
|---|---|---|
| 1 | $1.6 \times 10^7$ | $<10^2$ |
| 2 | $2.5 \times 10^8$ | $<10^2$ |
| 3 | $7.6 \times 10^8$ | $4.0 \times 10^5$ |
| 4 | $5.6 \times 10^7$ | $2.5 \times 10^7$ |
| 5 | $2.1 \times 10^7$ | $3.1 \times 10^7$ |

CP34 (NCIMB ACCESSION NO. 41185) Trial with HPC5 host

| | *Campylobacter* Control group: | Phage + *Campylobacter* group: (Average cfu/g) | | |
|---|---|---|---|---|
| Day | (Average cfu/g) | Dose $10^5$ pfu | Dose $10^7$ pfu | Dose $10^9$ pfu |
| 1 | $5.0 \times 10^6$ | $1.0 \times 10^3$ | $4.6 \times 10^2$ | $1.8 \times 10^5$ |
| 2 | $3.7 \times 10^6$ | $4.5 \times 10^3$ | $2.9 \times 10^4$ | $3.5 \times 10^4$ |
| 5 | $6.3 \times 10^6$ | $1.8 \times 10^4$ | $9.5 \times 10^2$ | $1.1 \times 10^5$ |

EXAMPLE 3

Disinfection of Chicken Using Bacteriophage

Direct disinfection of processed poultry products by phage may not be an effective means of controlling *Campylobacter* because phage require growth of their host for their replication. *Campylobacter* do not grow at refrigeration temperatures and atmospheric oxygen levels. However phage are well known for their ability to survive by remaining dormant for long periods, until growth of the host becomes possible. For example, on ingestion of contaminated material by a new host. Using a bacteriophage selected to bind *Campylobacter* efficiently and not bind to non-host bacteria, using the methods outlined, we have tested the ability of phage to reduce numbers of *Campylobacter* by adding them to non-growing *Campylobacter* on the surface of chicken skin.

This experiment was carried out using reference *C. jejuni* strain NCTC 12662 and phage CP8 (NCIMB ACCESSION NO. 41184). Six *Campylobacter* and phage negative birds were culled, plucked and skinned. Sections of skin measuring 2 cm$^2$ were placed in sterile Petri dishes. *Campylobacter* were added at different cell densities (between $10^6$ and $10^2$ cfu/ml) and incubated at room temperature for 1 hour. Phage were then applied at different densities ($10^7$, $10^5$ and $10^3$ pfu/ml) to give a range of different multiplicity of infection values between $10^5$ and $10^{-3}$. The chicken skin samples were then stored at 4° C. Phage and *Campylobacter* were enumerated at 24 h, 72 h and 120 h post inoculation and compared to controls inoculated with *Campylobacter* only. The samples were stomached in 20 ml MRD and counts of *Campylobacter* and phage were made as previously described. At the highest multiplicity of infection, there was a 1-log reduction (90%) in *Campylobacter* numbers compared to controls on each of the sample days. This represents the ability of the phage to absorb to *Campylobacter* and remain functional until growth of *Campylobacter* is possible due to suitable temperature and gaseous requirements. The phage can then lyse their hosts and produce a reduction in *Campylobacter* numbers.

The invention claimed is:

1. A method of reducing the level of *Campylobacter spp* infection of livestock comprising administering at least one bacteriophage selected from the group consisting of CP8 (NCIMB ACCESSION NO. 41184) and CP34 (NCIMB ACCESSION NO. 41185) in an effective amount to said livestock to reduce the number of *Campylobacter spp* present in the gastro-intestinal tract of said livestock.

2. A method as claimed in claim 1 in which the or each bacteriophage are administered to livestock at a range of between $10^2$ to $10^9$ pfu/ml.

3. A method as claimed in claim 2 in which the or each bacteriophage are administered to livestock at $10^5$ pfu/ml.

4. A method as claimed in claim 1 in which the livestock are chickens.

5. A method as claimed in claim 4 in which the livestock are broiler chickens.

6. A method as claimed in claim 1 in which the livestock is selected from the group consisting of ducks, turkeys, pigs, cattle, goats and sheep.

7. A method as claimed in claim 1 in which the or each bacteriophage are administered orally via ant-acid solution.

8. A method as claimed in claim 1 in which the or each bacteriophage are administered orally in the livestock's drinking water.

9. A method as claimed in claim 1 in which the or each bacteriophage are administered between 1 and 4 days before slaughter.

10. A method as claimed in claim 9 in which the or each bacteriophage are administered 2 days before slaughter.

11. A method as claimed in claim 1 in which the *Campylobacter spp* is *Campylobacter jejuni*.

12. A method as claimed in claim 1 in which the *Campylobacter spp* is *Campylobacter coli*.

* * * * *

SEQUENCE LISTING

```
<160> NUMBER OF SEQ ID NOS: 9

<210> SEQ ID NO 1
<211> LENGTH: 701
<212> TYPE: DNA
<213> ORGANISM: Artificial
<220> FEATURE:
<223> OTHER INFORMATION: Bacteriophage CP8

<400> SEQUENCE: 1
aaaattttta atcatataat tcaatggtaa tttattactc caatctattc tagattcatc      60
aaaaataatt ttcatattct tagttaaatt aggaaagtct ctgtgaacga atacacaatt     120
acatattctt actaaatgtt tattagcaac agactctgaa aattctgtat accattttga     180
aatatttgtc atacttatat ttaatttatc cgctatttct gcagttaaca tataatcttt     240
agttacgaag ttcattttaa ccccaaataa aataagccgg gtatgctacc atcattacta     300
cggctacgcc tgcgtaaact aagtcaaatg taaatctatt atcacctaat tttgatttga     360 agttttcat ttaatctcct ttatcttta atgaaataat tataatataa aataacttaa      420
atgtttctta aatattaaat attaaagttt atcaagataa taaatactct aaaaatacat     480
agaggccaaa atgtataaac tattattaga aaattctctt aaagagtcta caaacttaat     540
taacgaaggg tatagatgca gatttttacc aagttatgtt gggtgatatc ttaaaagata     600
```

```
aaatcaaatc atttataggg acatcatatt gctgaagttc aacctatgct gcaaccatct      660
ggctatgttt ttgcaagaca aagaaaccca agacacattt g                         701
```

<210> SEQ ID NO 2
<211> LENGTH: 22
<212> TYPE: DNA
<213> ORGANISM: Artificial
<220> FEATURE:
<223> OTHER INFORMATION: Bacteriophage CP8

<400> SEQUENCE: 2

```
gtctctgtga acgaatacac aa                                              22
```

<210> SEQ ID NO 3
<211> LENGTH: 22
<212> TYPE: DNA
<213> ORGANISM: Artificial
<220> FEATURE:
<223> OTHER INFORMATION: Bacteriophage CP8

<400> SEQUENCE: 3

```
gtagtataac gacttcaagt tg                                              22
```

<210> SEQ ID NO 4
<211> LENGTH: 433
<212> TYPE: DNA
<213> ORGANISM: Artificial
<220> FEATURE:
<223> OTHER INFORMATION: Bacteriophage CP8
<220> FEATURE:
<221> NAME/KEY: misc_feature
<222> LOCATION: (114)..(114)
<223> OTHER INFORMATION: "n" can be any nucleotide

<400> SEQUENCE: 4

```
aaataaaata caagacgaaa agaatcgaga acttgttaac aacattaaag aacttgaaaa      60
caaacccatt agaactgaaa caaaatacat agcagtcaag gattgtaaag ttcnaatatc     120
taaagtagac accaatatta cctcagctaa aggtatacct ttattttag gaaatatagg      180 taaaatacaa ttatctaatc aaaaataagg aatcactatg aaaattaaaa agttttatt      240 ggccttaata cccttatttt ttgtgggttg tactgcagtt agaaccgagt ttatttaccc     300
aaaaatacca gatgttaaag aaccacctat gacacaagat tataatctaa ctgtaataaa     360
aataaataat gtagaatatt attctttaag ccctgaagat gctaagattt tatcagagaa     420
ctggatcaag ttt                                                       433
```

<210> SEQ ID NO 5
<211> LENGTH: 21
<212> TYPE: DNA
<213> ORGANISM: Artificial
<220> FEATURE:
<223> OTHER INFORMATION: Bacteriophage CP8

<400> SEQUENCE: 5

```
gaatcgagaa cttgttaaca a                                               21
```

<210> SEQ ID NO 6
<211> LENGTH: 20
<212> TYPE: DNA
<213> ORGANISM: Artificial
<220> FEATURE:
<223> OTHER INFORMATION: Bacteriophage CP8

-continued

```
<400> SEQUENCE: 6
cttggtggat actgtgttct                                                  20

<210> SEQ ID NO 7
<211> LENGTH: 101
<212> TYPE: DNA
<213> ORGANISM: Artificial
<220> FEATURE:
<223> OTHER INFORMATION: Bacteriophage CP8

<400> SEQUENCE: 7
caaaagcaac ttataaagaa ctgagtttac ctttccttga gttggttttt tatttgattt      60
atctataaaa actttgttta atgttaaaaa atttttgggt a                        101

<210> SEQ ID NO 8
<211> LENGTH: 16
<212> TYPE: DNA
<213> ORGANISM: Artificial
<220> FEATURE:
<223> OTHER INFORMATION: Bacteriophage M13

<400> SEQUENCE: 8
gtaaaacgac ggccag                                                      16

<210> SEQ ID NO 9
<211> LENGTH: 24
<212> TYPE: DNA
<213> ORGANISM: Artificial
<220> FEATURE:
<223> OTHER INFORMATION: Bacteriophage M13

<400> SEQUENCE: 9
agcggataac aatttcacac agga                                             24
```